US012714656B2

(12) United States Patent
Wang et al.

(10) Patent No.: US 12,714,656 B2
(45) **Date of Patent: *Aug. 25, 2026**

(54) AQUEOUS ORAL CARE IODIDE-CONTAINING COMPOSITIONS, METHODS, AND KITS

(71) Applicant: Solventum Intellectual Properties Company, Maplewood, MN (US)

(72) Inventors: Yizhong Wang, Woodbury, MN (US); Ta-Hua Yu, Woodbury, MN (US); Joel D. Oxman, Minneapolis, MN (US); Richard P. Rusin, Woodbury, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 301 days.

This patent is subject to a terminal disclaimer.

(21) Appl. No.: 18/469,859

(22) Filed: Sep. 19, 2023

(65) Prior Publication Data

US 2024/0000675 A1 Jan. 4, 2024

Related U.S. Application Data

(63) Continuation of application No. 17/158,326, filed on Jan. 26, 2021, now Pat. No. 11,793,734, which is a continuation of application No. PCT/IB2019/056376, filed on Jul. 25, 2019.

(60) Provisional application No. 62/703,976, filed on Jul. 27, 2018.

(51) Int. Cl.

| | |
|---|---|
| ***A61K 8/21*** | (2006.01) |
| ***A61K 8/46*** | (2006.01) |
| ***A61K 33/18*** | (2006.01) |
| ***A61K 33/38*** | (2006.01) |
| ***A61P 1/02*** | (2006.01) |
| ***A61Q 11/00*** | (2006.01) |
| ***A61Q 11/02*** | (2006.01) |

(52) U.S. Cl.

CPC ................. *A61K 8/21* (2013.01); *A61K 8/46* (2013.01); *A61Q 11/00* (2013.01); *A61Q 11/02* (2013.01); *A61K 2800/5424* (2013.01); *A61K 2800/5426* (2013.01); *A61K 2800/92* (2013.01)

(58) Field of Classification Search

CPC .. A61Q 11/00; A61K 8/21; A61K 2800/5424; A61K 2800/5426; A61K 2800/92; A61K 6/20

See application file for complete search history.

(56) References Cited

U.S. PATENT DOCUMENTS

| | | | |
|---|---|---|---|
| 2,981,640 | A | 4/1961 | Hill |
| 3,567,823 | A | 3/1971 | Yamaga et al. |
| 4,012,839 | A | 3/1977 | Hill |
| 6,165,494 | A | 12/2000 | Picciano |
| 6,461,161 | B1 | 10/2002 | Ngo et al. |
| 6,923,990 | B2 | 8/2005 | Capelli |
| 7,465,693 | B2 | 12/2008 | Greer et al. |
| 8,968,709 | B2 | 3/2015 | Yang et al. |
| 2002/0156130 | A1 | 10/2002 | Melman |
| 2005/0142077 | A1 | 6/2005 | Zimmer et al. |
| 2006/0134020 | A1 | 6/2006 | Robinson et al. |
| 2010/0247456 | A1 | 9/2010 | Niederman et al. |
| 2014/0079651 | A1 | 3/2014 | Sagel et al. |
| 2018/0168955 | A1 | 6/2018 | Shabo |

FOREIGN PATENT DOCUMENTS

| | | | |
|---|---|---|---|
| JP | 2003171914 | A | 6/2003 |
| JP | 4229431 | B2 | 2/2009 |
| WO | 2017149326 | A1 | 9/2017 |
| WO | 2018092889 | A1 | 5/2018 |

OTHER PUBLICATIONS

Ashby, "Inorganic Chemistry of Defensive Peroxidases in the Human Oral Cavity", Journal of Dental Research, 2008, vol. 87, No. 10, pp. 900-914.

Dentistry IQ, "SDI Introduces Riva Star Silver Diamine Fluoride Desensitizer," Apr. 23, 2018, [online], [retrieved on Nov. 30, 2023]. Retrieved from the internet: <https://www.dentistryiq.com/print/content/16367834>, 3 pages.

Garg, "Potassium Iodide Reversal of Silver Diamine Fluoride Staining: A Case Report," Operative Dentistry, May/Jun. 2019, vol. 44, No. 3, pp. 221-226.

Hamama, "Effect of silver diamine fluoride and potassium iodide on residual bacteria in dentinal tubules", Australian Dental Journal, 2015, vol. 60, pp. 80-87, XP002795502.

International Search Report and Written Opinion for PCT/IB2019/056376, dated Nov. 27, 2019, 4 pages.

International Search Report and Written Opinion for PCT/IB2019/057203, dated Jan. 29, 2020, 4 pages.

Koizumi, "Effect Of A Silver Diamine Fluoride And Potassium Iodide-Based Desensitizing And Cavity Cleaning Agent On Bond Strength To Dentine", International Journal Of Adhesion & Adhesives, 2016, vol. 68, pp. 54-61.

New USA SDF Market Entry, The Silver Bulletin, Aug. 1, 2018, vol. 4, [online], [retrieved on Nov. 30, 2023]. Retrieved from the internet: <http://www.elevateoralcare.com/silverbulletinv4>, 6 pages.

Nguyen, "Potassium Iodide. The Solution to Silver Diamine Fluoride Discoloration," Advances in Dentistry and Oral Health, Jun. 2017, vol. 5, No. 1, pp. 001-006.

Zhao, "Effect of Silver Diamine Fluoride and Potassium Iodide Treatment on Secondary Caries Prevention and Tooth Discolouration in Cervical Glass Ionomer Cement Restoration," International Journal of Molecular Sciences, Feb. 2017, vol. 18, pp. 340-1-340-12.

*Primary Examiner* — Tracy Liu

(57) ABSTRACT

An aqueous oral care one-part composition (e.g., solution), a kit that includes such composition (e.g., solution), and methods (e.g., a method of providing fluoride to a patient's tooth surface), wherein the oral care composition (e.g., solution) includes: silver cations; iodide anions; fluoride anions; and water.

17 Claims, 1 Drawing Sheet

AQUEOUS ORAL CARE IODIDE-CONTAINING COMPOSITIONS, METHODS, AND KITS

CROSS-REFERENCE TO RELATED APPLICATIONS

This application is a continuation application of Ser. No. 17/158,326, filed Jan. 26, 2021, which is a continuation of PCT/IB2019/056376, filed Jul. 25, 2019, which claims the benefit of U.S. Provisional Application No. 62/703,976, filed Jul. 27, 2018, the disclosures of which are incorporated by reference in their entireties herein.

BACKGROUND

Silver and fluoride ions are well-known for treating tooth surfaces to address hypersensitivity and arrest dental caries.

Fluoride treatment involves the application of fluoride to a tooth surface with the formation of fluorapatite and calcium fluoride. There are two major in-office fluoride treatment methods currently in use.

One treatment method uses a fluoride gel/foam in a tray. This method requires several grams of fluoride gel stored in a tray that is then placed into a patient's mouth onto the teeth. This tray is left in the mouth with the gel/foam in contact with the teeth for 1 to 4 minutes. The gel/foam formulation is an aqueous system that includes 2% sodium fluoride. This material requires the use of suction to pull the extra gel out of the mouth to avoid unnecessary high amounts of fluoride ingestion.

Another treatment method is a dental fluoride varnish. Most fluoride varnishes on the market are rosin/ethanol based formulations with a hydrophobic nature. The varnish is painted on the teeth and remains in place for several hours to allow for the fluoride to be released from the composition. Typically, dentists use fluoride varnishes for in-office fluoride treatment. Most dental fluoride varnishes include 5% sodium fluoride. The dose of varnish is about 0.5 gram. Dental varnishes place much smaller amounts of fluoride into a patient's mouth compared to fluoride gel/foams. Thus, fluoride ingestion is less with fluoride varnishes. Also, fluoride varnishes are easier to apply as they are simply painted on a patient's teeth; however, fluoride varnish treatments are more labor intensive than gel treatments and fluoride varnish treatments leave the patient with an unpleasant "dirty teeth" feeling.

Stable aqueous solutions containing both silver and fluoride ions are needed. One such solution includes silver diamine fluoride (SDF); however, SDF is also known for turning the tooth surface black when it is exposed to light.

Compositions that are as simple to apply to teeth as varnishes and work in time periods as short as gel/foam formulations are desired, particularly those compositions that include silver and fluoride, but do not stain the tooth surface upon exposure to light.

SUMMARY OF THE DISCLOSURE

The present disclosure provides aqueous oral care compositions (e.g., solutions) and methods of treating (e.g., methods of providing fluoride to a patient's tooth surface). Such compositions are one-part compositions.

Such one-part compositions (e.g., solutions) can be used as in-office oral care solutions (e.g., as fluoride treatment solutions). They can be formulated into a solution that can be painted on a tooth surface if desired. They can provide similar fluoride efficacy to that of varnishes in the shorter periods of time of gel/foam formulations.

In one embodiment, the present disclosure provides an aqueous oral care one-part composition (e.g., solution) that includes: silver cations; iodide anions; fluoride anions; and water.

In certain embodiments, an aqueous oral care one-part composition (e.g., solution) includes: 13-17 wt-% silver cations; iodide anions; and 2.25-3.0 wt-% fluoride anions; wherein the weight percentages are based on the total weight of the composition (e.g., solution).

In certain embodiments, the molar ratio of silver to iodide ions is less than 0.42:1, and water is less than 41.2 wt-%, based on the total weight of the composition (e.g., solution). In certain embodiments, the molar ratio of silver to iodide ions is at least 0.09:1 and less than 0.42:1.

In certain embodiments, the oral care composition (e.g., solution) forms a precipitate (e.g., AgI) upon contact with additional water or saliva.

In another embodiment, the present disclosure provides a method of providing fluoride to a patient's tooth surface. The method involves applying an aqueous oral care one-part composition (e.g., solution) as disclosed herein to the patient's tooth surface.

In another embodiment, the present disclosure provides a method of reducing the incidence of dental caries. The method involves applying an aqueous oral care one-part composition (e.g., solution) as disclosed herein to the patient's tooth surface.

In another embodiment, the present disclosure provides a method of reducing dentin sensitivity and/or root sensitivity (e.g., during cavity treatment and/or on an exposed root) in a patient in need thereof. The method involves applying an aqueous oral care one-part composition (e.g., solution) as disclosed herein to the patient's tooth surface.

In another embodiment, the present disclosure provides a method of treating a patient's tooth surface. The method involves applying an aqueous oral care one-part composition as disclosed herein to the patient's tooth surface. In certain embodiments, the method further includes applying a dental restorative to the treated tooth surface.

In another embodiment, the present disclosure provides a kit that includes an aqueous oral care one-part composition (e.g., solution) as described herein and an applicator.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the phrases "at least one" and "one or more." The phrases "at least one of" and "comprises at least one of" followed by a list refers to any one of the items in the list and any combination of two or more items in the list.

The term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

DETAILED DESCRIPTION OF ILLUSTRATIVE EMBODIMENTS

Figure 1:
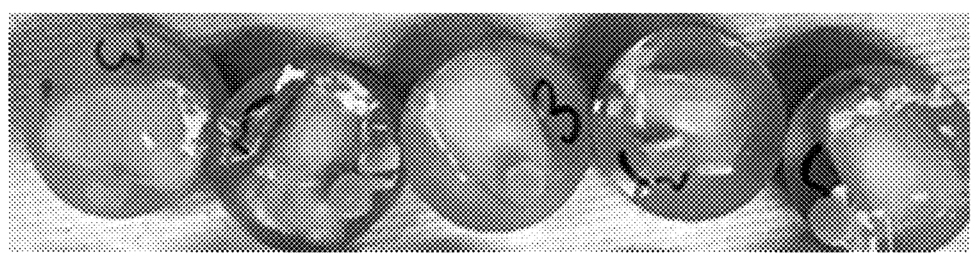
FIG. 1 is a photograph of the five replicate bovine teeth samples of Comparative Example C-20 (CONTROL); which had no silver fluoride solution treatment prior to treatment with a RMGI liner material (VITREBOND Plus Light Cure Glass Ionomer Liner/Base); it shows no discoloration.

The present disclosure provides aqueous oral care compositions (e.g., solutions). Such compositions are one-part compositions.

The present disclosure also provides methods, such as providing fluoride to a patient's tooth surface, as well as reducing the incidence of dental caries, for example. Such methods involve applying an aqueous oral care one-part composition (e.g., solution such as a fluoride treatment solution) as described herein to the patient's tooth surface.

In certain embodiments, applying an aqueous oral care one-part composition (e.g., solution) includes painting the oral care one-part composition (e.g., solution) on the patient's tooth surface.

In certain embodiments, applying an aqueous oral care one-part composition (e.g., solution) includes dispensing the oral care one-part composition (e.g., solution) into a dental tray and attaching the tray having the oral care one-part composition (e.g., solution) therein to the patient's tooth surface. In certain embodiments, the dental tray includes an orthodontic aligner treatment tray.

In certain embodiments, an aqueous oral care one-part composition (e.g., solution) includes: silver cations; iodide anions; fluoride anions; and water.

In certain embodiments, the silver ions (also referred to herein as silver cations) are present in an amount of at least 12.2 percent by weight (wt-%), at least 13 wt-%, or at least 13.5 wt-%, wherein the weight percentages are based on the total weight of the composition (e.g., solution). In certain embodiments, the silver cations are present in an amount of up to 20 wt-%, up to 19 wt-%, up to 18 wt-%, or up to 17 wt-%, wherein the weight percentages are based on the total weight of the composition (e.g., solution).

In certain embodiments, the source of silver cations is selected from silver fluoride, silver chloride, silver nitrate, silver iodide, silver diamine fluoride, and combinations thereof.

In certain embodiments, the fluoride ions (also referred to herein as fluoride anions) are present in an amount of at least 2.0 wt-%, at least 2.1 wt-%, at least 2.2 wt-%, or at least 2.25 wt-%, wherein the weight percentages are based on the total weight of the composition (e.g., solution). In certain embodiments, the fluoride anions are present in an amount of up to 4.0 wt-%, up to 3.9 wt-%, up to 3.8 wt-%, up to 3.5 wt-%, or up to 3.0 wt-%, wherein the weight percentages are based on the total weight of the composition (e.g., solution).

In certain embodiments, the source of fluoride anions is selected from silver fluoride, silver diamine fluoride, sodium fluoride, ammonium fluoride, potassium fluoride, amine fluoride, and combinations thereof.

In certain embodiments, an aqueous oral care one-part composition (e.g., solution) includes: 12.2-20 wt-% silver cations; and 2.0-4.0 wt-% fluoride anions; wherein the weight percentages are based on the total weight of the composition (e.g., solution). In certain embodiments, the oral care one-part composition (e.g., solution) includes: 13-17 wt-% silver cations; and 2.25-3.0 wt-% fluoride anions.

In certain embodiments, the molar ratio of silver to iodide ions is less than 0.42:1. In certain embodiments, the molar ratio of silver to iodide ions is at least 0.09:1.

In certain embodiments, the source of iodide ions (also referred to herein as iodide anions) is selected from ammonium iodide, sodium iodide, potassium iodide, silver iodide, and combinations thereof. In certain embodiments, the source of iodide ions includes ammonium iodide and optionally a secondary source of iodide ions selected from sodium iodide, potassium iodide, silver iodide, and combinations thereof. In certain embodiments, the source of iodide ions includes ammonium iodide and a secondary source of iodide ions selected from sodium iodide, potassium iodide, silver iodide, and combinations thereof.

In certain embodiments, an aqueous oral care one-part composition (e.g., solution) includes water in an amount of at least 20 wt-%, based on the total weight of the composition (e.g., solution).

In certain embodiments, the amount of water is less than 41.2 wt-%, based on the total weight of the composition (e.g., solution).

Upon contact with additional water or saliva in the oral environment, the oral care one-part composition (e.g., solution) forms a precipitate (i.e., a solid formed from the composition (e.g., solution)). The precipitate includes AgI, which provides antibacterial effect.

In certain embodiments, an oral care one-part composition (e.g., solution) includes: 12.2-20 wt-% (or 13-17 wt-%) silver cations; and 2.0-4.0 wt-% (or 2.25-3.0 wt-%) fluoride anions; wherein the weight percentages are based on the total weight of the composition (e.g., solution); and iodide anions, wherein a molar ratio of silver to iodide ions is at least 0.09:1 and less than 0.42:1; wherein the oral care one-part composition (e.g., solution) forms a precipitate upon contact with additional water or saliva.

Oral care one-part compositions (e.g., solutions) of the present disclosure are aqueous compositions (e.g., solutions), although they may include a small amount of one or more organic solvents. Examples of organic solvents are selected from ethanol, isopropanol, dimethyl sulfoxide (DMSO), isoprene sulfone (IS), butadiene sulfone (BS), piperylene sulfone (PS), ethyl acetate, methyl acetate, isopropyl acetate, acetone, methyl ethyl ketone (MEK), methyl isobutyl ketone (MIBK), and combinations thereof.

Preferably, the aqueous oral care one-part compositions (e.g., solutions) are free of organic solvents that function as liquid carriers (as opposed to organic solvents that are used as carriers/solvents for flavorants or sweeteners). For example, certain additives may be provided as a solution or dispersion in an organic solvent as a liquid carrier. If there is any organic solvent (that functions as a liquid carrier) present in aqueous oral care one-part compositions (e.g., solutions) of the present disclosure, it is present in an amount of less than 5 wt-%, based on the total weight of the aqueous composition (e.g., solution).

Preferably, aqueous oral care one-part compositions (e.g., solutions) of the present disclosure do not stain teeth, which is particularly surprising because of the potential oxidation of silver. This can be determined by combining an oral care composition (e.g., solution) in a ratio of 3:1 with a 1% phosphate solution and exposing it to a blue LED light with wavelength of 430-480 nm and output of approximately 1500 mW/cm$^2$ (−10%/+20%), such as that commercially available under the Tradename 3M ELIPAR DEEPCURE-S LED curing light (available from 3M Company, St. Paul, MN), for 20 seconds to see whether the mixture forms a dark (e.g., black, brown, or grey) precipitate.

Significantly, compositions (e.g., solutions) of the present disclosure do not turn (discolor) to a dark color such as black, brown, or grey after being precipitated and exposed to LED light. While not being bound by theory, it is believed that the AgI, fluoride ions, and excess iodide ions, complex with calcium in the tooth, and thereby avoid discoloration.

Preferably, aqueous oral care compositions of the present disclosure are solutions that are shelf stable for at least 6 months, or at least 1 year without precipitation (detectable to the human eye) particularly when in a sealed container. Thus, aqueous oral care solutions of the present disclosure are clear (i.e., transparent or translucent without any cloudiness) for at least 6 months, or at least 1 year until contacted with additional water or saliva.

Additional Optional Active Agents

Aqueous oral care one-part compositions (e.g., solutions) of the present disclosure can also contain one or more active agents in addition to a source of fluoride. When included, the one or more additional active agents usually, but not always, include one or more active agents that are active in the oral cavity against disorders, diseases, or conditions of the teeth, gums, cheeks, tongue, roof of the mouth, and the like.

Examples of additional active agents that can be employed include one or more other fluorine-containing compounds, such as sodium monofluorophosphate, stannous fluoride, calcium fluoride, strontium fluoride, zinc fluoride, zinc potassium fluoride, ammonium fluoride, potassium magnesium fluoride, and combinations thereof.

Examples of additional active agents that can be employed include one or more whitening agents, anticalculus agents, remineralization agents, stannous sources, antimicrobial agents, antioxidants, saliva stimulating agents, breath freshening agents, antiplaque agents, anti-inflammatory agents, $H_2$ antagonists, desensitizing agents, nutrients, and proteins. Various combinations of such additional active agents may be used if desired. When employed, one or more additional active agents will be typically used in amounts sufficient to achieve their intended effect.

When employed, the whitening agents can be a wide variety of suitable whitening agents. The whitening agents can include, for example, a peroxide whitening agent, a non-peroxide whitening agent, or both. Peroxide whitening agents include hydrogen peroxide, peroxide of alkali or alkaline earth metals, such as sodium peroxide, potassium peroxide, lithium peroxide, magnesium peroxide, calcium peroxide, barium peroxide, and the like, glyceryl hydrogen peroxide, alkyl hydrogen peroxide, dialkyl peroxide, peroxy acids or peroxy acid salts, benxoyl peroxide, urea peroxide, and the like. Hydrogen peroxide is most common. Non-peroxide whitening agents include chlorine dioxide, chlorites, and hypochlorites. Chlorites and hyperchlorites are typically in the form of alkali or alkaline earth metal salts, such as salts of lithium, potassium, sodium, magnesium, calcium, or barium. Colorants, titanium dioxide, and hydroxyapatite can also be used.

When employed, the anticalculus agents can be a wide variety of suitable anticalculus agents. The anticalculus agents can include, for example, phosphates, polyphosphates, such as pyrophosphates, polyolefin sulfonates, polyolefin phosphates, diphosphonates, phosphonoalkane carboxylic acids, and salts thereof, typically alkali metal or ammonium salts.

When employed, the remineralization agents can be a wide variety of suitable remineralization agents. The remineralization agents can include, for example, materials that release calcium ions, phosphorous-containing ions, or both, such as calcium phosphate (e.g., mono-, di-, and/or tricalcium phosphate), hydroxyapatite, calcium carbonate, and the like.

Examples of materials that release calcium ions are calcium salts that are water soluble, such as those selected from calcium chloride, calcium nitrate, calcium gluconate, calcium lactate gluconate, calcium acetate, hydrates thereof, and combinations thereof. In certain embodiments, the calcium salt is selected from calcium chloride, calcium nitrate, hydrates thereof, and combinations thereof.

A calcium salt can also be used to modulate the fluoride release profile.

When employed, the stannous sources can be a wide variety of suitable sources of stannous ions. The stannous ion sources can include, for example, stannous halides, organic stannous carboxylate salts, such as stannous formate, stannous acetate, stannous gluconate, stannous lactate, stannous tartrate, and stannous citrate. When the fluoride source is stannous fluoride, it can also function as a stannous source.

When employed, the antimicrobial agents can include a wide variety of orally acceptable antimicrobial agents. Examples include triclosan, 8-hydroxyquinoline, zinc ion, stannous ion, cupric compounds, phthalic acid and salts thereof, quaternary ammonium compounds, sanguinarine, salicylanilide, salicylic acid, thymol, eugenol, neomycin, kanamycin, clindamycin, amoxicillin, tetracycline, doxycycline, minocycline, metronidazole, chlorohexidine, and the like.

When employed, the antioxidants can be a wide variety of orally acceptable antioxidants. Examples include butylated hydroxy anisone, butylated hydroxy toluene, vitamin A, carotenoids, vitamin E, flavonoids, polyphenols, ascorbic acid or salts thereof, chlorophyll, melatonin, and the like.

When employed, the saliva stimulants can be a wide variety of orally acceptable saliva stimulants. Examples include citric acid, lactic acid, succinic acid, ascorbic acid, adipic acid, fumaric acid, and tartaric acid.

When employed, the breath freshening agents can be a wide variety of orally acceptable breath freshening agents. Examples include zinc salts such as zinc salts of gluconate, citrate, chlorite, alpha-ionone, and the like.

When employed, the antiplaque agents can be a wide variety of orally acceptable antiplaque agents. Examples include stannous salts, salts of copper, magnesium or strontium, dimethicone copolyols, such as cetyl dimethicone copolyol, papain, glucamylase, glucose oxidase, urea, calcium lactate, calcium glycerophosphate, strontium polyacrylates, and the like. Further examples of antiplaque agents include biofilm inhibition agents, particularly those described in U.S. Pat. No. 8,968,709 (Yang et al.).

When employed, the anti-inflammatory agents can be a wide variety of orally acceptable anti-inflammatory agents. Examples include steroids such as flucinolone and hydrocortisone, non-steroidal anti-inflammatory drugs such as ketorolac, flurbiprofen, ibuprofen, naproxen, indomethacin, diclofenac, etodolac, indomethacin, sulindac, tomlmetin, ketoprofen, fenoprofen, piroxicam, nabumetone, acetyl salicylic acid, salicylic acid, diflunisal, meclofenamate, mefenamic acid, oxyphenbutazone, phenylbutazone, and the like.

When employed, the $H_2$ antagonists can be a wide variety of orally acceptable $H_2$ antagonists. Examples include cimetidine, etinidine, ranitidine, tiotidine, lupitidine, denetidine, famotidine, roxatidine, pifatidine, lamtidine, zaltidine, nizatidine, mifentidine, ramixotidine, loxtidine, bisfentidine, sufotidine, ebrotidine, impromdine, and the like.

When employed, the desensitizing agents can be a wide variety of orally acceptable desensitizing agents. Examples include potassium citrate, potassium chloride, potassium tartrate, potassium bicarbonate, potassium oxalate, potassium nitrate, strontium salts, arginine, acetyl salicylic acid or salts thereof, salicylic acid or salts thereof, codeine, acetaminophen, and the like.

When employed, the nutrients can be a wide variety of orally acceptable nutrients. Examples include vitamins, such as vitamins C, D, thiamine, riboflavin, folic acid, nicotinamide, niacin, pyridoxine, bioflavonoids, and the like, supplements, such as amino acids, lipotropics, fish oil, polyunsaturated fatty acids, eicosapentanoic acid, docosahexanic acid, coenzyme Q10, ubiquinone, minerals such as potassium, and the like.

When employed, the proteins can include a wide variety of orally acceptable proteins. Examples include milk proteins, peroxide producing enzymes, amylase, papain, glucoamylase, glucose oxidase, and the like.

Buffers

Aqueous oral care one-part compositions (e.g., solutions) of the present disclosure can include a pharmaceutically acceptable buffer. The type and amount of such buffer is selected to provide an oral care composition (e.g., solution) with a pH of at least 5.5, at least 6, or at least 6.5. In certain embodiments, the type and amount of such buffer is selected to provide an oral care composition (e.g., solution) with a pH of up to 9, up to 8.5, up to 7.5, or up to 7. In certain embodiments, the type and amount of such buffer is selected to provide an oral care composition (e.g., solution) with a pH of 6.5 to 7.5, or a pH of 7.0. A wide variety of suitable pharmaceutically acceptable buffers can be included. Examples include acetate (e.g., sodium acetate), sodium carbonate, citrate (e.g., sodium citrate), tartrate, glycylglycine, histidine, glycine, lysine, arginine, sodium dihydrogen phosphate, disodium hydrogen phosphate, sodium phosphate, tris(hydroxymethyl)-aminomethane, or mixtures thereof.

Thickeners

In certain embodiments, aqueous oral care one-part compositions (e.g., solutions) of the present disclosure include a thickener to provide a composition (e.g., solution) with a suitable viscosity to allow for the desired method of application. For example, a suitable thickener in a sufficient amount may be used to achieve a composition (e.g., solution) viscosity adequate to maintain the composition (e.g., solution) in an inverted mouthpiece tray applicator for up to four minutes (typical time for a professionally applied fluoride treatment), and yet be fluid enough to have acceptable handling characteristics for the dental operator (e.g., when dispensing into a dental tray applicator). Or, a suitable thickener in a sufficient amount may be used to achieve a viscosity adequate to paint on a tooth surface.

In certain embodiments, the type and amount of thickener is selected to provide an oral care composition (e.g., solution) with a viscosity of at least 0.5 Pascal seconds at a shear rate of 1.0/second. In certain embodiments, a type and amount of thickener is selected to provide an oral care composition (e.g., solution) with a viscosity of up to 500 Pascal seconds at a shear rate of 1.0/second.

In certain embodiments, a thickener is present in an oral care one-part composition (e.g., solution) in an amount of less than 2.5 wt-%, based on the total weight of the aqueous composition (e.g., solution). In certain embodiments, a thickener is present in an amount of at least 0.5 wt-%, based on the total weight of the aqueous composition (e.g., solution).

Suitable thickeners are typically those that are generally safe for human ingestion (FDA approved for internal use), do not bind fluoride ions, and do not significantly affect the bioavailability of fluoride ions.

In certain embodiments, the thickener is selected from natural gums, non-acid cellulose derivatives (e.g., hydroxyethyl cellulose), inorganic fillers (e.g., colloidal silica, fumed silica, alumina, titania, and zinc oxide), alkylene oxide polymers (e.g., polyethylene glycol, polypropylene glycol, and copolymers of polyethylene glycol and polypropylene glycol), non-acid modified starches, and combinations thereof.

Optional Additives

In certain embodiments, aqueous oral care compositions (e.g., solutions) of the present disclosure include one or more optional additives including flavoring agents (i.e., flavorants) and sweeteners. Other optional additives include surfactants. Various combinations of such additives may be used if desired.

In certain embodiments, aqueous oral care compositions (e.g., solutions) of the present disclosure include a sweetener. A wide variety of orally acceptable sweeteners can be used. Common sweeteners include xylitol, sorbitol, sucralose, aspartame, saccharin, usually sodium saccharine, and the like. When present, a sweetener can be used in any suitable amount, most often in an amount sufficient to impart a pleasant sweetness to the composition (e.g., solution). The suitable amount is typically 0.5 wt-% to 15 wt-%, based on the total weight of the aqueous composition (e.g., solution).

In certain embodiments, aqueous oral care compositions (e.g., solutions) of the present disclosure include a flavoring agent. A wide variety of orally acceptable flavoring agents can be used. Common flavoring agents include peppermint oil, spearmint oil, cherry flavor, citric acid, orange flavor, vanilla, strawberry flavor, coconut flavor, and bubble gum flavor. When present, a flavoring agent can be used in any suitable amount, most often in an amount sufficient to impart a desired flavor to the composition (e.g., solution). The suitable amount is typically 1 wt-% to 4 wt-%, based on the total weight of the aqueous composition (e.g., solution).

In certain embodiments, aqueous oral care compositions (e.g., solutions) of the present disclosure include a surfactant. Typically, such surfactant is an anionic surfactant, examples of which include polysorbate, glycerol, polyglycerol-based surfactant, or combinations thereof. When present, a surfactant can be used in any suitable amount, most often in an amount sufficient to impart wettability. A suitable amount is typically 0.1 wt-% to 5.0 wt-%, based on the total weight of the aqueous composition (e.g., solution).

Kits

In certain embodiments, aqueous oral care compositions (e.g., solutions) of the present disclosure are included in kits. Typically, such kit includes an applicator (e.g., dental brush, cotton tip swab) for the oral care composition (e.g., solution). Such applicator may be integrated into a container having the oral care composition (e.g., solution) therein.

In certain embodiments, the oral care composition (e.g., solution) is provided in individual sealed unit dose containers. In use, the seals of such individual sealed unit dose containers are broken and the composition (e.g., solution) picked up with the applicator and the composition (e.g., solution) applied to a tooth surface.

In certain embodiments, the oral care composition (e.g., solution) is provided in a multi-dose container. In use, a drop of the composition (e.g., solution) can be dispensed onto a tray, piece of plastic, piece of paper, dish, well, pan, etc., and the composition (e.g., solution) picked up with the applicator and the composition (e.g., solution) applied to a tooth surface.

In certain embodiments, the kit may further include one or more of a dental restorative, a tray, a dish, a well, or a pan. Examples of dental restorative include, but are not limited to, an adhesive, primer, cement, liner, sealant, amalgam, resin, resin composite, glass ionomer, resin-modified glass ionomer, glass-ceramic, ceramic, metal, plastic, or combination thereof Methods of Making and Using An aqueous oral care composition (e.g., solution) of the present disclosure can be made using any techniques known to one of skill in the art. In certain embodiments, the components are added together into water and dissolved, in no particular order. Alternatively, the order of addition can be important in obtaining a composition (e.g., solution). For example, in certain embodiments, the source(s) of silver and fluoride (e.g., AgF) is dissolved in water first and then the source of iodide is added. Alternatively, each component can be dissolved in water separately and then combined to form an aqueous oral care composition (e.g., solution).

In certain embodiments, an aqueous oral care composition (e.g., solution) of the present disclosure is used in a method of providing fluoride to a patient's tooth surface. The method includes applying the aqueous oral care composition (e.g., solution) described herein to the patient's tooth surface.

In certain embodiments, an aqueous oral care composition (e.g., solution) of the present disclosure is used in a method of reducing the incidence of dental caries (e.g., by preventing or arresting dental caries) in a patient in need thereof. The method includes applying the aqueous oral care composition (e.g., solution) described herein to the patient's tooth surface.

In certain embodiments, an aqueous oral care composition (e.g., solution) of the present disclosure is used in a method of reducing dentin sensitivity and/or root sensitivity (e.g., during cavity treatment and/or on an exposed root) in a patient in need thereof. The method includes applying the aqueous oral care composition (e.g., solution) described herein to the patient's tooth surface.

In certain embodiments, an aqueous oral care composition (e.g., solution) of the present disclosure is used in a method of treating a patient's tooth surface. The method includes applying the aqueous oral care one-part composition (e.g., solution) disclosed herein to the patient's tooth surface to form a treated tooth surface, and optionally applying a dental restorative to the treated tooth surface.

In certain embodiments, a patient's tooth surface that is treated with a method as described herein includes enamel, dentin, cementum, root, or combinations thereof.

In certain embodiments of the methods described above, applying includes painting the oral care composition (e.g., solution) on the patient's tooth surface. In certain embodiments of the methods described above, applying includes dispensing the oral care composition (e.g., solution) into a dental tray (e.g., an orthodontic aligner treatment tray) and attaching the tray having the oral care composition (e.g., solution) therein to the patient's tooth surface.

In certain embodiments of the methods described above, the oral care composition (e.g., solution) is subsequently dried (e.g., using flowing air) after being applied to the tooth surface. The source of flowing air can be delivered from an air compressor that delivers at high pressure limits of 115 psi. One example of a suitable air compressor is an Osprey Compressor from RAMVAC (models OSP22, OSP13, OSP23, OSP24, OSP25, OSP28) commercially available from Dental EZ Integrated Solutions of Malvern, PA, or Patterson Dental of St. Paul, MN. Another example of an air compressor is AirStar Neo air compressors by AIR TECHNIQUES (Models such as AirStar 10 Neo, AirStar 21 Neo) commercially available from Patterson Dental of St. Paul, MN. Alternatively, the pressurized gas device could be a typical air/water syringe found in most dental offices for delivering pressurized air. Optimum air pressure with a typical dental air/water syringe is 40-80 psi. Such syringes are used to dry the teeth or to blow scaled calculus off the teeth. One example of such a syringe is a Johnson-Promident 3-Way Air/Water Syringe commercially available from Patterson Dental Supply Inc., Patterson Item #: 404-1893. Regardless, the gas is blown by some pressurized gas source, and could be air or some other inert gas or gas mixture. For example, the gas could be nitrogen, helium, argon, carbon dioxide, or nitrous oxide. The source of pressurized gas could be part of a permanently installed "in-house" pressurized air/gas system or a hand held, self-contained canister.

In certain embodiments of the methods described above, water is subsequently applied to the oral care composition (e.g., solution) after being applied to the tooth surface to form a precipitate thereon (i.e., on the tooth surface). In certain embodiments of the methods described above, saliva is subsequently allowed to contact the oral care composition (e.g., solution) on the tooth surface to form a precipitate thereon (i.e., on the tooth surface).

In certain embodiments of the methods described above, the oral care composition (e.g., solution) is subsequently wiped with cotton, paper, and any other wiping material to remove excess oral care composition (e.g., solution) on the tooth surface after being applied to the tooth surface.

In certain embodiments of the methods described above, the methods further include placing a dental restorative on the tooth surface having the oral care composition (e.g., solution) applied thereto (either before or after the composition (e.g., solution) is dried, rinsed off, wiped off, and/or a precipitate is formed on the tooth surface). Examples of dental restorative include, but are not limited to, an adhesive (such as 3M SCOTCHBOND Universal Adhesive (available from 3M Company of St. Paul, MN, USA), primer, cement (such as 3M RelyX UNICEM 2 AUTOMIX Self-Adhesive Resin Cement, available from 3M Company of St. Paul, MN, USA), liner (such as 3M ESPE VITREBOND Plus Light Cure Glass Ionomer Liner/Base), sealant, amalgam, resin, resin composite (3M FILTEK Z250 Universal Restorative), glass ionomer (such as 3M KETAC Universal APLICAP Glass Ionomer Restorative), resin-modified glass ionomer (such as RelyX Luting Plus RMGI Cement), glass-ceramic, ceramic, metal, plastic, or combination thereof. Examples 10-14 illustrate the use of several of these dental restoration materials.

EXEMPLARY EMBODIMENTS

Embodiment 1 is an aqueous oral care one-part fluoride composition (e.g., solution) comprising: silver cations; iodide anions; fluoride anions; and water.

Embodiment 2 is the oral care composition (e.g., solution) of embodiment 1 comprising ammonium iodide.

Embodiment 3 is the oral care composition (e.g., solution) of embodiment 2 further comprising a secondary source of iodide anions selected from sodium iodide, potassium iodide, silver iodide, and combinations thereof.

Embodiment 4 is the oral care composition (e.g., solution) of any of the preceding embodiments wherein the molar ratio of silver to iodide ions is less than 0.42:1.

Embodiment 5 is the oral care composition (e.g., solution) of any of the preceding embodiments wherein the molar ratio of silver to iodide ions is at least 0.09:1.

Embodiment 6 is the oral care composition (e.g., solution) of any of the preceding embodiments comprising: 12.2-20 wt-% silver cations; and 2.0-4.0 wt-% fluoride anions; wherein the weight percentages are based on the total weight of the composition (e.g., solution).

Embodiment 7 is the oral care composition (e.g., solution) of embodiment 6 comprising: 13-17 wt-% silver cations; iodide anions; and 2.25-3.0 wt-% fluoride anions.

Embodiment 8 is the oral care composition (e.g., solution) of any of the preceding embodiments which forms a precipitate (e.g., AgI) upon contact with additional water or saliva.

Embodiment 9 is the oral care composition (e.g., solution) of any of the preceding embodiments comprising a source of silver cations selected from silver fluoride, silver chloride, silver nitrate, silver iodide, silver diamine fluoride, and combinations thereof.

Embodiment 10 is the oral care composition (e.g., solution) of any of the preceding embodiments comprising a source of fluoride anions selected from silver fluoride, silver diamine fluoride, sodium fluoride, ammonium fluoride, potassium fluoride, amine fluoride, and combinations thereof.

Embodiment 11 is the oral care composition (e.g., solution) of any of the preceding embodiments further comprising a pharmaceutically acceptable buffer.

Embodiment 12 is the oral care composition (e.g., solution) of any of the preceding embodiments further comprising a thickener.

Embodiment 13 is the oral care composition (e.g., solution) of embodiment 12 wherein the thickener is present in an amount of less than 2.5 wt-%.

Embodiment 14 is the oral care composition (e.g., solution) of any of the preceding embodiments which has a pH of 5.5 to 9.

Embodiment 15 is the oral care composition (e.g., solution) of any of the preceding embodiments comprising less than 5 wt-% organic solvent.

Embodiment 16 is the oral care composition (e.g., solution) of embodiment 15 wherein the organic solvent is selected from ethanol, isopropanol, dimethyl sulfoxide (DMSO), isoprene sulfone (IS), butadiene sulfone (BS), piperylene sulfone (PS), ethyl acetate, methyl acetate, isopropyl acetate, acetone, methyl ethyl ketone (MEK), methyl isobutyl ketone (MIBK), and combinations thereof.

Embodiment 17 is the oral care composition (e.g., solution) of any of the preceding embodiments comprising less than 41.2 wt-%, and in certain embodiments at least 20 wt-% water, based on the total weight of the composition (e.g., solution).

Embodiment 18 is the oral care composition (e.g., solution) of any of the preceding embodiments further comprising one or more active agents.

Embodiment 19 is the oral care composition (e.g., solution) of embodiment 18 wherein the one or more active agents comprise whitening agents, anticalculus agents, remineralization agents, stannous sources, antimicrobial agents, antioxidants, saliva stimulating agents, breath freshening agents, antiplaque agents, anti-inflammatory agents, $H_2$ antagonists, desensitizing agents, nutrients, proteins, or combinations thereof.

Embodiment 20 us the oral care composition (e.g., solution) of any of the preceding embodiments further comprising a flavoring agent.

Embodiment 21 is the oral care composition (e.g., solution) of any of the preceding embodiments further comprising a sweetener.

Embodiment 22 is the oral care composition (e.g., solution) of any of the preceding embodiments further comprising calcium cations.

Embodiment 23 is the oral care composition (e.g., solution) of embodiment 22 comprising a source of calcium cations selected from calcium chloride, calcium nitrate, calcium gluconate, calcium lactate gluconate, calcium acetate, hydrates thereof, and combinations thereof.

Embodiment 24 is the oral care composition (e.g., solution) of any of the preceding embodiments further comprising a surfactant.

Embodiment 25 is the oral care composition (e.g., solution) of embodiment 24 wherein the surfactant is an anionic surfactant.

Embodiment 26 is the oral care composition (e.g., solution) of embodiment 25 wherein the anionic surfactant is selected from polysorbate, glycerol, polyglycerol-based surfactant, and combinations thereof.

Embodiment 27 is the oral care composition (e.g., solution) of any of the preceding embodiments which does not stain teeth.

Embodiment 28 is the oral care composition (e.g., solution) of embodiment 27, which when combined 3:1 with a 1% phosphate composition (e.g., solution) and exposing it to a blue LED light with wavelength of 430-480 nm and output of approximately 1500 mW/cm$^2$ for 20 seconds (to see whether the mixture turned forms a dark (e.g., black, brown, or grey) precipitate).

Embodiment 29 is the oral care composition (e.g., solution) of any of the preceding embodiments which is shelf stable for at least 6 months, or at least 1 year.

Embodiment 30 is a method of providing fluoride to a patient's tooth surface, the method comprising applying the aqueous oral care one-part composition (e.g., solution) of any of the preceding embodiments to the patient's tooth surface.

Embodiment 31 is a method of reducing the incidence of dental caries (e.g., by preventing or arresting dental caries) in a patient in need thereof, the method comprising applying an aqueous oral care one-part composition (e.g., solution) of any of embodiments 1 through 29 to the patient's tooth surface.

Embodiment 32 is a method of reducing dentin sensitivity and/or root sensitivity (e.g., during cavity treatment and/or on an exposed root) in a patient in need thereof, the method comprising applying an aqueous oral care one-part composition (e.g., solution) of any of embodiments 1 through 29 to the patient's tooth surface.

Embodiment 33 is a method of treating a patient's tooth surface, the method comprising applying an aqueous oral care one-part composition (e.g., solution) of any of embodiments 1 through 29 to the patient's tooth surface.

Embodiment 34 is the method of any of embodiments 30 through 33 wherein the patient's tooth surface comprises enamel, dentin, cementum, root, or combinations thereof.

Embodiment 35 is the method of any of embodiments 30 through 34 wherein applying comprises painting the oral care composition (e.g., solution) on the patient's tooth surface.

Embodiment 36 is the method of any of embodiments 30 through 35 wherein applying comprises dispensing the oral care composition (e.g., solution) into a dental tray (e.g., an orthodontic aligner treatment tray) and attaching the tray having the oral care solution therein to the patient's tooth surface.

Embodiment 37 is the method of any of embodiments 30 through 36 wherein the oral care composition (e.g., solution) is subsequently dried (e.g., using flowing air) after being applied to the tooth surface.

Embodiment 38 is the method of any of embodiments 30 through 37 wherein water is subsequently applied to the oral care composition (e.g., solution) after being applied to the tooth surface to form a precipitate thereon (i.e., on the tooth surface).

Embodiment 39 is the method of any of embodiments 30 through 37 wherein saliva is subsequently allowed to contact the oral care composition (e.g., solution) on the tooth surface to form a precipitate thereon (i.e., on the tooth surface).

Embodiment 40 is the method of any of embodiments 30 through 39 further comprising placing a dental restorative on the tooth surface having the oral care composition (e.g., solution) applied thereto (either before or after the composition (e.g., solution) is dried, wiped off, rinsed off, and/or a precipitate is formed on the tooth surface).

Embodiment 41 is the method of embodiment 42 wherein the dental restorative comprises an adhesive, primer, cement, liner, sealant, amalgam, resin, resin composite, glass ionomer, resin-modified glass ionomer, glass-ceramic, ceramic, metal, plastic, or combination thereof.

Embodiment 42 is a kit comprising an aqueous oral care one-part composition (e.g., solution) of any one of embodiments 1 through 29 and an applicator (e.g., dental brush, cotton tip swab).

Embodiment 43 is the kit of embodiment 42 wherein the oral care composition (e.g., solution) is provided in individual sealed unit dose containers.

Embodiment 44 is the kit of embodiment 42 wherein the oral care composition (e.g., solution) is provided in a multidose container.

Embodiment 45 is the kit of any of embodiments 42 through 44 wherein the applicator is integrated into the container having the oral care composition (e.g., solution) therein.

Embodiment 46 is the kit of any of embodiments 42 through 45 further comprising a dental restorative.

Embodiment 47 is the kit of embodiment 46 wherein the dental restorative comprises an adhesive, primer, cement, liner, sealant, amalgam, resin, resin composite, glass ionomer, resin-modified glass ionomer, glass-ceramic, ceramic, metal, plastic, or combination thereof.

Embodiment 48 is the kit of any of embodiments 42 through 47 further comprising a tray, a dish, a well, or a pan.

Embodiment 49 is a method of making an aqueous oral care one-part composition (e.g., solution) of any one of embodiments 1 through 29 comprising combining a source of silver and a source of fluoride (which may be the same, e.g., AgF) in water and dissolving therein; and adding a source of iodide and dissolving therein to form an aqueous oral care composition (e.g., solution).

EXAMPLES

Objects and advantages of this disclosure are further illustrated by the following examples, but the particular materials and amounts thereof recited in these examples, as well as other conditions and details, should not be construed to unduly limit this disclosure. These examples are merely for illustrative purposes only and are not meant to be limiting on the scope of the appended claims.

TABLE 1

| Materials | | |
|---|---|---|
| Description | Source | Location |
| Silver fluoride (AgF) | Oakwood Chemical | West Columbia, SC |
| Ammonium iodide ($NH_4I$) | Honeywell Specialty Chemical | Seelze, Germany |
| Ammonium thiocyanate ($NH_4SCN$) | Alfa Aesar | Ward Hill, MA |
| Disodium hydrogen citrate sesquihydrate | Alfa Aesar | Ward Hill, MA |
| Sodium carbonate | EMD | Gibbstown, NJ |
| Potassium phosphate monobasic | Sigma Aldrich | St Louis, MO |
| Ammonium chloride ($NH_4Cl$) | VWR | West Chester, PA |
| Potassium sulfate | J.T. Baker | Phillipsburg, NJ |
| Silver iodide | Sigma Aldrich | St Louis, MO |
| Silver diamine fluoride solution 38%, commercially available as ADVANTAGE ARREST silver diamine fluoride | Elevate Oral Care | West Palm Beach, FL |

Example Preparation

The general sample preparation procedure was as follows. Exact percent quantities are described in the tables below. An amount of 0.5 gram of the silver compound was added to an appropriately sized plastic tube. The full amount of water (described in tables below) was added to the container to dissolve the silver compound. The remaining component(s) were added to the silver compound solution. Initially, this addition caused a precipitate to occur. For examples of the present disclosure, the continued addition of the full amount of the remaining components caused the precipitate to re-dissolve, as the one-part composition (e.g., solution) was prepared. For comparative examples, the continued addition of the full amount of the remaining components did not re-dissolve the precipitate, the precipitate remained.

TABLE 2

| Comparative Examples C-1 to C-7 | | | | | | | |
|---|---|---|---|---|---|---|---|
| Components | C-1 | C-2 | C-3 | C-4 | C-5 | C-6 | C-7 |
| AgF | 16.7 | 16.7 | 16.7 | 16.7 | 16.7 | 18.4 | 18.5 |
| Disodium hydrogen citrate sesquihydrate | 50.0 | 0 | 0 | 0 | 0 | 0 | 0 |
| Sodium carbonate | 0 | 50.0 | 0 | 0 | 0 | 0 | 0 |
| Potassium phosphate monobasic | 0 | 0 | 50.0 | 0 | 0 | 0 | 0 |
| $NH_4Cl$ | 0 | 0 | 0 | 50.0 | 0 | 22.1 | 0 |
| $NH_4SCN$ | 0 | 0 | 0 | 0 | 0 | 0 | 22.2 |
| $NH_4I$ | 0 | 0 | 0 | 0 | 0 | 22.8 | 22.2 |
| Potassium sulfate | 0 | 0 | 0 | 0 | 50.0 | 0 | 0 |
| Deionized (DI) water | 33.3 | 33.3 | 33.3 | 33.3 | 33.3 | 36.8 | 37.0 |
| Total (%) | 100 | 100 | 100 | 100 | 100 | 100 | 100 |
| Ag % | 14.2 | 14.2 | 14.2 | 14.2 | 14.2 | 15.6 | 15.7 |
| Fluoride % | 2.5 | 2.5 | 2.5 | 2.5 | 2.5 | 2.8 | 2.8 |
| Ag/SCN mole ratio | 0 | 0 | 0 | 0 | 0 | 0 | 0.5 |
| Ag/I mole ratio | 0 | 0 | 0 | 0 | 0 | 0.92 | 0.95 |
| Precipitate formed initially | Yes | Yes | Yes | Yes | Yes | Yes | Yes |
| Precipitate dissolved with all chemicals in | No | No | No | No | No | No | No |

TABLE 3

Examples Ex-1 to Ex-4 and Comparative Example C-8; With $NH_4I$; Water Less than 41%

| Component | Ex-1 | Ex-2 | Ex-3 | Ex-4 | C-8 |
|---|---|---|---|---|---|
| AgF | 19.2 | 17.9 | 16.7 | 15.6 | 14.7 |
| $NH_4I$ | 57.7 | 53.6 | 50.0 | 46.9 | 44.1 |
| $H_2O$ | 23.1 | 28.6 | 33.3 | 37.5 | 41.2 |
| Total (%) | 100 | 100 | 100 | 100 | 100 |
| Ag % | 16.4 | 15.2 | 14.2 | 13.3 | 12.5 |
| Fluoride % | 2.9 | 2.7 | 2.5 | 2.3 | 2.2 |
| Ag/I mole ratio | 0.38 | 0.38 | 0.38 | 0.38 | 0.38 |
| Precipitate formed initially | Yes | Yes | Yes | Yes | Yes |
| Precipitate dissolved with all chemicals in | Yes | Yes | Yes | Yes | No |

TABLE 4

Example Ex-5 and Comparative Examples C-9 to C-11; With $NH_4I$; Silver to Iodide Mole Ratio Less than 0.42 to Dissolve the Precipitate and Form a Solution

| Component | Ex-5 | C-9 | C-10 | C-11 |
|---|---|---|---|---|
| AgF | 17.2 | 18.2 | 19.2 | 20.8 |
| $NH_4I$ | 51.7 | 49.1 | 46.2 | 41.7 |
| $H_2O$ | 31.0 | 32.7 | 34.6 | 37.5 |
| Total (%) | 100 | 100 | 100 | 100 |
| Ag/Iodide mole ratio | 0.38 | 0.42 | 0.48 | 0.57 |
| Ag % | 14.7 | 15.5 | 16.4 | 17.7 |
| Fluoride % | 2.6 | 2.7 | 2.9 | 3.1 |
| Precipitate formed initially | Yes | Yes | Yes | Yes |
| Precipitate dissolved with all chemicals in | Yes | No | No | No |

TABLE 5

Example Ex-6

| Component | EX-6 |
|---|---|
| AgI | 31.0 |
| AgF | 0 |
| $NH_4I$ | 31.4 |
| $NH_4F$ | 4.9 |
| DI water | 32.7 |
| Total % | 100 |
| Ag % | 14.3 |
| Total Iodine % | 44.4 |
| Total Fluoride % | 2.5 |
| Precipitate formed initially | Yes |
| Precipitate dissolved with all chemicals in | Yes |

Example 7

Silver diamine fluoride water solution (38%) (commercially available as ADVANTAGE ARREST from Elevate Oral Care of West Palm Beach, Florida, USA) was used as source of silver and fluoride. An amount of 0.1 gram of silver diamine fluoride solution was mixed with 0.248 gram of $NH_4I$, the mixture released ammonia and a little bit of $NH_4I$ did not dissolve and a precipitate was initially formed. The mixture then became a clear solution. This example demonstrated that silver diamine fluoride solution can be used as the source of silver and fluoride and be converted to the inventive composition with the addition of the appropriate amount of counter ion.

Light Sensitivity of Examples

The following examples demonstrated that solutions of the inventive composition do not turn (discolor) to a dark color such as black, brown, or grey after (1) being precipitated with the addition of a buffer solution (to mimic saliva in the oral environment), and (2) exposure to light using 3M ELIPAR DEEPCURE-S LED curing light.

Comparative Example 12 (C-12)

An amount of 25 mg of silver diamine fluoride solution (ADVANTAGE ARREST silver diamine fluoride solution (38%)) was mixed with 40 mg of 1% $KH_2PO_4$ water solution. The mixture formed a precipitate. The mixture was exposed to a blue LED light using 3M ELIPAR DEEP-CURE-S LED curing light, with wavelength around 450 nm and output approximately 1500 $mW/cm^2$ for 20 seconds, the mixture turned black.

Example 8

An amount of 23 mg of EX-2 solution was mixed with 43 mg of 1% $KH_2PO_4$ water solution. The mixture formed a precipitate. The mixture was exposed to a blue LED light using 3M ELIPAR DEEPCURE-S LED curing light, with wavelength around 450 nm and output approximately 1500 $mW/cm^2$ for 20 seconds, the mixture did NOT turn (discolor) to a dark color (e.g., black, brown, or grey).

Example 9

An amount of 48 mg of EX-7 solution was mixed with 100 mg of 1% $KH_2PO_4$ water solution. The mixture formed a precipitate. The mixture was exposed to a blue LED light using 3M ELIPAR DEEPCURE-S LED curing light, with wavelength around 450 nm and output approximately 1500 $mW/cm^2$ for 20 seconds, the mixture did NOT turn (discolor) to a dark color (e.g., black, brown, or grey).

Methods of Using the Inventive Composition

The following examples illustrate embodiments of the use of the inventive composition incorporated into various dental restoration procedures.

Preparation of Test Surface

Bovine teeth samples were prepared in the following manner to serve as a test surface for Example treatments. Bovine teeth were held in an acrylic mold and polished with 120 grit sand paper to expose the dentin, then polished with 320 grit sandpaper to smooth the dentin surface.

Preparatory Example A

The composition of Example 6 (EX-6, above) was again prepared as follows. An amount of 42.24 grams of ammonium iodide and 6.59 grams of ammonium fluoride were mixed with 44 grams of deionized water to form a solution. Then 41.8 grams of silver iodide was added to the solution and mixed well at room temperature to form a one-part composition (e.g., solution). This solution of Example 6 was used to treat the polished bovine tooth surface which had been prepared as described above. The treatment process included: applying a drop of the silver fluoride solution of Example 6 to the tooth surface by using a mini dental adhesive brush to rub the solution onto the dried dentin surface for 10 seconds, waiting for 1 minute to let the solution penetrate dentin surface. The treated tooth surface was then rinsed with water and air dried to remove excess water and be ready to use as Preparatory Example A for the next Example Treatments described below.

Comparative Preparatory Example B

Silver diamine fluoride (SDF) water solution (38%) (commercially available as ADVANTAGE ARREST from Elevate Oral Care of West Palm Beach, Florida, USA) was used as the Comparative Preparatory Example B. This solution was used to treat the polished bovine tooth surface which had been prepared as described above. The treatment process included: applying a drop of the commercially available SDF solution to the tooth surface by using a mini dental adhesive brush to rub the solution onto the dried dentin surface for 10 seconds, waiting for 1 minute to let the solution penetrate dentin surface. The treated tooth surface was then rinsed with water and air dried to remove excess water and be ready to use as Preparatory Example B for the next Comparative Example Treatments described below.

Control Preparatory Example C

The Control Preparatory Example C was a prepared bovine tooth, placed in an acrylic mold and polished as described above, and rinsed with water and dried, but it was NOT treated with either the Example 6 or commercially available silver diamine fluoride solution.

Example 10 (EX-10) Adhesion of Glass Ionomer to a Tooth Treated with Example 6

Example 10 was prepared by placing a second mold consisting of a 2 mm thick sheet of TEFLON over the prepared bovine tooth of Preparatory Example A that had been treated with Example 6, held in the acrylic mold. The second mold included a 4.8 mm hole that was positioned over the prepared and treated tooth (dentin) surface. A glass ionomer restorative material (3M KETAC Universal APLICAP Glass Ionomer Restorative, available from 3M Company of St. Paul, MN, USA) was filled into the hole of the second mold and cured in 37° C. and 95% humidity chamber for 20 minutes and stored in 37° C. water for 24 hours to harden. This created a cylindrical "button" that was 2 mm high and 4.8 mm in diameter, on the surface of the prepared tooth, which could be tested for adhesion strength to the tooth surface. The bonding strength of the glass ionomer (GI) material button to the prepared and treated tooth surface was tested on an INSTRON 5944 tester (Instron Corporation of Norwood, MA, USA) operating in shear mode. Five (5) replicate bovine teeth were thus prepared and tested. The mean value of adhesion strength is reported below in Table 6.

Comparative Example 13 (C-13)—Adhesion of Glass Ionomer to a Tooth Treated with Commercially Available Silver Diamine Fluoride (SDF)

Comparative Example C-13 was prepared in exactly the same manner as Example 10 with the exception of using Comparative Preparatory Example B instead of Preparatory Example A. In other words, silver diamine fluoride (SDF) solution was used instead of Example 6 to treat the prepared tooth surface. On each of five (5) replicates, cylindrical "buttons" made of GI material were created and tested as described in Example 10.

Comparative Example 14 (C-14; Control)—Adhesion of Glass Ionomer to a Polished Tooth (Dentin) Surface that was Untreated Comparative Example C-14 (Control) was prepared in exactly the same manner as Example 10 with the exception of no treatment with a silver fluoride solution before adhering the GI material to the dentin surface. On each of five (5) replicates, cylindrical "buttons" made of GI material were created and tested as described in Example 10.

TABLE 6

Adhesion of Self-Curing Glass Ionomer (GI) Material

| Dentin adhesion of GI Material | C-14 (Control) | C-13 (SDF) | EX-10 |
|---|---|---|---|
| Average (MPa) | 2.5 | 3.2 | 4.9 |
| Stdev. | 0.9 | 0.9 | 1.6 |

Example 11 (EX-11) Adhesion of Resin Modified Glass Ionomer (RMGI) Cement to a Tooth Treated with Example 6

Example EX-11 was prepared in exactly the same manner as Example 10 (EX-10) with the exception that the hole in the second mold was filled with RelyX™ Luting Plus Cement (Resin Modified Glass Ionomer (RMGI) cement), available from 3M Company of St. Paul, MN, USA, instead of the 3M KETAC Universal APLICAP Glass Ionomer Restorative. This created a cylindrical "button" of RMGI material adhered to the prepared and treated tooth (dentin) surface. On each of five (5) replicates, cylindrical "buttons" made of RMGI material were created and tested as described in Example 10. The mean value of adhesion strength is reported below in Table 7.

Comparative Example 15 (C-15)—Adhesion of RMGI to a Tooth Treated with Commercially Available Silver Diamine Fluoride (SDF)

Comparative Example C-15 was prepared in exactly the same manner as Comparative Example 13 with the exception of using RelyX Luting Plus Cement (Resin Modified Glass (RMGI) Ionomer cement) instead of the 3M KETAC Universal APLICAP Glass Ionomer Restorative. On each of five (5) replicates, cylindrical "buttons" made of RMGI material were created and tested as described in Example 10. The mean value of adhesion strength is reported below in Table 7.

Comparative Example 16 (C-16; Control)—Adhesion of RMGI to a Polished Tooth (Dentin) Surface that was Untreated Comparative Example C-16 was prepared in exactly the same manner as Comparative Example 14 (Control) with the exception of using RelyX Luting Plus Cement (Resin Modified Glass (RMGI) Ionomer cement) instead of the 3M KETAC Universal APLICAP Glass Ionomer Restorative. On each of five (5) replicates, cylindrical "buttons" made of RMGI material were created and tested as described in Example 10. The mean value of adhesion strength is reported below in Table 7.

TABLE 7

| Adhesion of Self-Curing Resin Modified Glass Ionomer (RMGI) Material | | | |
|---|---|---|---|
| Dentin adhesion of RMGI Material | C-16 (Control) | C-15 (SDF) | EX-11 |
| Average (MPa) | 3.7 | 5.3 | 5.5 |
| Stdev. | 0.65 | 1.2 | 1.3 |

Example 12 (EX-12) Adhesion of Resin Cement to a Tooth Treated with Example 6

Example EX-12 was prepared in exactly the same manner as Example EX-10 with the exception that the hole in the second mold was filled with 3M RelyX UNICEM 2 AUTOMIX Self-Adhesive Resin Cement, available from 3M Company of St. Paul, MN, USA, instead of the 3M KETAC Universal APLICAP Glass Ionomer Restorative. This created a cylindrical "button" of Resin Cement material adhered to the prepared and treated tooth (dentin) surface. On each of five (5) replicates, cylindrical "buttons" made of Resin Cement material were created and tested as described in Example 10. The mean value of adhesion strength is reported below in Table 8.

Comparative Example 17 (C-17)—Adhesion of Resin Cement to a Tooth Treated with Commercially Available Silver Diamine Fluoride (SDF)

Comparative Example C-17 was prepared in exactly the same manner as Comparative Example 13 with the exception of using 3M RelyX UNICEM 2 AUTOMIX Self-Adhesive Resin Cement instead of the 3M KETAC Universal APLICAP Glass Ionomer Restorative. On each of five (5) replicates, cylindrical "buttons" made of Resin Cement material were created and tested as described in Example 10. The mean value of adhesion strength is reported below in Table 8.

Comparative Example 18 (C-18; Control)—Adhesion of Resin Cement to a Polished Tooth (Dentin) Surface that was Untreated Comparative Example C-18 (Control) was prepared in exactly the same manner as Comparative Example 14 (Control) with the exception of using 3M RelyX UNICEM 2 AUTOMIX Self-Adhesive Resin Cement instead of the 3M KETAC Universal APLICAP Glass Ionomer Restorative. On each of five (5) replicates, cylindrical "buttons" made of Resin Cement material were created and tested as described in Example 10. The mean value of adhesion strength is reported below in Table 8.

TABLE 8

| Adhesion of Resin Cement | | | |
|---|---|---|---|
| Dentin adhesion of Resin Cement Material | C-18 (Control) | C-17 (SDF) | EX-12 |
| Average (MPa) | 4.6 | 3.2 | 5.4 |
| Stdev. | 1.0 | 0.9 | 3.0 |

Example 13 (EX-13) Adhesion of RMGI Liner Material to a Tooth Treated with Example 6

Figure 3:
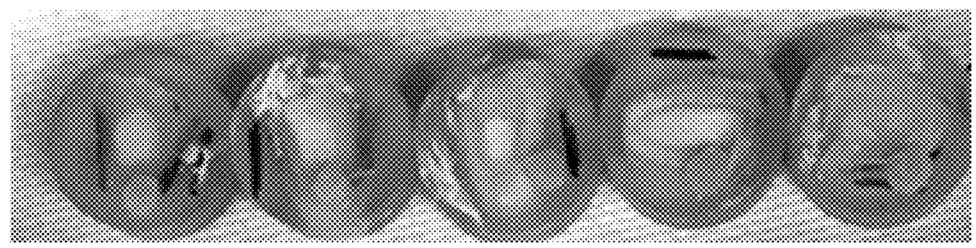
FIG. 3 is a photograph of the five replicate bovine teeth samples of Example EX-13, an illustrative embodiment of the disclosure, which shows no black discoloration after teeth being treated with the one-part composition followed by treatment with a RMGI liner material (VITREBOND Plus Light Cure Glass Ionomer Liner/Base).

Example 13 (EX-13) was prepared by placing a piece of masking tape with a 4.8 mm hole punched in it over the prepared bovine tooth of Preparatory Example A that had been treated with Example 6, held in the acrylic mold. The hole-punched masking tape controlled the diameter and thickness of the RMGI liner treatment. Following the instructions for use, 3M ESPE VITREBOND Plus Light Cure Glass Ionomer Liner/Base product (available from 3M Company of St. Paul, MN, USA) was applied to the tooth surface at the hole punched in the masking tape. This RMGI liner material was then cured with 3M ELIPAR DEEPCURE-S LED (blue) curing light, with wavelength around 450 nm and output approximately 1500 mW/cm$^2$ for 20 seconds There was no dark (e.g., black, brown, or grey) discoloration of the tooth surface observed for all five replicate EX-13 samples. Next, 3M SCOTCHBOND Universal Adhesive (available from 3M Company of St. Paul, MN, USA) was applied to the treated tooth surface followed again by blue LED light curing for 20 seconds. At this point the second mold consisting of a 2 mm thick sheet of TEFLON was placed over the above prepared and treated bovine tooth surface, held in the acrylic mold. The second mold included the 4.8 mm hole, described above, that was positioned over the prepared and treated tooth (dentin) surface. A dental composite material (3M FILTEK Z250 Universal Restorative, available from 3M Company of St. Paul, MN, USA) was filled into the hole of the second mold and cured with blue LED light for 20 seconds, then stored in 37° C. water for 24 hours to harden. This created a cylindrical "button" that was 2 mm high and 4.8 mm in diameter on the surface of the prepared tooth which could be used to test the adhesion strength RMGI liner material to the tooth surface. The bonding strength was tested on an INSTRON 5944 tester (Instron Corporation of Norwood, MA, USA) operating in shear mode. Five (5) replicate bovine teeth were thus prepared and tested. The mean value of adhesion strength is reported below in Table 9. See FIG. 3 for a photograph of the five replicates of Example 13 (EX-13), which shows no discoloration, staining, or blackening of the treated bovine teeth. For tracking purposes, each of the five replicates were marked with the number "3" in black ink at the edge of each sample; this should not be confused with any kind of staining or discoloration.

Comparative Example 19 (C-19)—Adhesion of RMGI Liner Material to a Tooth Treated with Commercially Available Silver Diamine Fluoride (SDF)

Figure 2:
FIG. 2 is a photograph of the five replicate bovine teeth samples of Comparative Example C-19, which shows the black discoloration effect of silver diamine fluoride when applied to a tooth prior to treatment with a RMGI liner material (VITREBOND Plus Light Cure Glass Ionomer Liner/Base).

Comparative Example C-19 was prepared in exactly the same manner as Example 13 (EX-13) with the exception of using Comparative Preparatory Example B instead of Preparatory Example A. In other words, silver diamine fluoride (SDF) solution was used instead of Example 6 to treat the prepared tooth surface, to which was subsequently applied the RMGI liner material (VITREBOND Plus Light Cure Glass Ionomer Liner/Base), followed by SCOTCHBOND Universal Adhesive and then 3M FILTEK Z250 Universal Restorative dental composite to form the "button." Each of five (5) replicates were tested as described in Example 13 and results are reported in Table 9. It should be noted that each of the C-19 replicates turned a black discoloration after blue light curing of the VITREBOND Plus Light Cure Glass Ionomer Liner/Base. See FIG. 2 for a photograph of the five replicates of Comparative Example C-19, which shows the blackish discoloration of the bovine teeth first treated with silver diamine fluoride (SDF). For tracking purposes, each of the five replicates were marked with the number "2" in black ink at the edge of each sample; this should not be confused with the black discoloration that results from the SDF reaction with light.

Comparative Example 20 (C-20; Control)—Adhesion of RMGI Liner Material to a Polished Tooth (Dentin) Surface that was Untreated Comparative Example C-20 (Control) was prepared in exactly the same manner as Example 13 with the exception of no treatment of the polished tooth surface (dentin) with a silver fluoride solution before adhering the RMGI liner material (VITREBOND Plus Light Cure Glass Ionomer Liner/Base), followed by SCOTCHBOND Universal Adhesive and then finally the 3M FILTEK Z250 Universal Restorative dental composite to form the "button" on the dentin surface. On each of five (5) replicates, cylindrical "buttons" were created and tested as described in Example 13, with results shown in Table 9. See FIG. 1 for a photograph of the five replicates of Comparative Example 20 (C-20), which shows no discoloration, staining, or blackening of the treated bovine teeth. For tracking purposes, each of the five replicates were marked with the number "1" in black ink at the edge of each sample; this should not be confused with any kind of staining or discoloration.

TABLE 9

| Adhesion of RMGI Liner Material | | | |
|---|---|---|---|
| Dentin adhesion of RMGI Liner Material | C-20 (Control) | C-19 (SDF) | EX-13 |
| Average (MPa) | 10.9 | 14.1 | 10.2 |
| Stdev. | 4.1 | 1.5 | 2.5 |
| Tooth discoloration after photocuring | None | Turned Blackish Grey | None |

Example 14 (EX-14) Adhesion of Dental Adhesive to a Tooth Treated with Example 6

Example EX-14 was prepared by applying 3M SCOTCHBOND Universal Adhesive (available from 3M Company of St. Paul, MN, USA) to the treated tooth surface of Preparatory Example A, followed by curing with 3M ELIPAR DEEPCURE-S LED (blue) curing light, with wavelength around 450 nm and output approximately 1500 mW/cm$^2$ for 20 seconds. There was no dark (e.g., black, brown, or grey) discoloration of the tooth surface observed for all five replicate EX-14 samples. Next, the second mold consisting of a 2 mm thick sheet of TEFLON was placed over the above prepared and treated bovine tooth surface, held in the acrylic mold. The second mold included the 4.8 mm hole, described above, that was positioned over the prepared and treated tooth (dentin) surface. A dental composite material (3M FILTEK Z250 Universal Restorative, available from 3M Company of St. Paul, MN, USA) was filled into the hole of the second mold and cured with blue LED light for 20 seconds, then stored in 37° C. water for 24 hours to harden. This created a cylindrical "button," that was 2 mm high and 4.8 mm in diameter, on the surface of the prepared and treated tooth which could be used to test the adhesion strength of the SCOTCHBOND Universal (dental) Adhesive to the tooth surface. The bonding strength was tested on an INSTRON 5944 tester (Instron Corporation of Norwood, MA, USA) operating in shear mode. Five (5) replicate bovine teeth were thus prepared and tested. The mean value of adhesion strength is reported below in Table 10.

Comparative Example 21 (C-21)—Adhesion of Dental Adhesive to a Tooth Treated with Commercially Available Silver Diamine Fluoride (SDF)

Comparative Example C-21 was prepared in exactly the same manner as Example 14 with the exception of using Comparative Preparatory Example B instead of Preparatory Example A. In other words, silver diamine fluoride (SDF) solution was used instead of Example 6 to treat the prepared tooth surface, to which was subsequently applied SCOTCHBOND Universal Adhesive and then 3M FILTEK Z250 Universal Restorative dental composite to form the "button." Each of five (5) replicates were tested as described in Example 14, with results reported in Table 10. It should be noted that each of the C-21 replicates turned a black discoloration after blue light curing of the SCOTCHBOND Universal Adhesive.

Comparative Example 22 (C-22; Control)—Adhesion of Dental Adhesive to a Polished Tooth (Dentin) Surface that was Untreated Comparative Example C-22 (Control) was prepared in exactly the same manner as Example 14 (EX-14) with the exception of no treatment of the polished tooth surface (dentin) with a silver fluoride solution before applying dental adhesive SCOTCHBOND Universal Adhesive, followed by the 3M FILTEK Z250 Universal Restorative dental composite to form the "button" on the dentin surface. On each of five (5) replicates, cylindrical "buttons" were created and tested as described in Example 14, with results shown in Table 10.

TABLE 10

| Adhesion of Dental Adhesive to treated Teeth | | | |
|---|---|---|---|
| Dentin adhesion of Dental Adhesive | C-22 (Control) | C-21 (SDF) | EX-14 |
| Average (MPa) | 21.8 | 18.0 | 17.6 |
| Stdev. | 3.9 | 5.0 | 6.1 |
| Tooth discoloration after photocuring | None | Turned Blackish Grey | None |

Solution Stability Testing

Example 6 (EX-6) was used to assess the long-term solution stability of the disclosure. In each sample 1 mL of Example 6 solution was placed in a plastic test tube, which was sealed in a glass vial to prevent evaporation. The samples were stored for several months under the temperature conditions described below and tested periodically at designated time points. Each sample was tested for General Appearance, Precipitation with $KH_2PO_4$, and Color Change (Black staining). Additional select samples were also tested for fluoride content over time.

Appearance Testing

Appearance was tested by visually observing any precipitation formed in the solution (naturally) or color change during aging/stability study.

Precipitation Testing

A precipitation test was performed by inducing precipitation by the introduction of one drop of 1% monopotassium phosphate ($KH_2PO_4$) and observing any formed precipitate.

Color Change (Staining) Testing

Color change was performed by exposing the precipitate formed with the addition of $KH_2PO_4$ to blue LED light using 3M ELIPAR DEEPCURE-S LED curing light, with wavelength around 450 nm and output approximately 1500 mW/cm2 for 20 seconds. This test was performed to look for dark (e.g., black, brown, or grey) discoloration of the formed precipitate, which is characteristic of the discoloration of silver diamine fluoride+$KH_2PO_4$ precipitate when exposed to light.

Fluoride Content Testing

Fluoride level in parts per million (ppm) was measured for select samples using a Mettler Toledo T70 titrator. The Cole Parmer fluoride electrode was first calibrated with parts per million (ppm) fluoride standards with TISAB III before measuring samples for fluoride content. Total Ionic Strength Adjustment Buffer (TISAB) III concentrate solution is for use with fluoride ion selective electrodes and is available from Sigma Aldrich. The fluoride ion selective electrode was placed in the titrator cup of diluted TISAB III solution and allowed to equilibrate for 30 seconds before analyzing each sample. The fluoride content in ppm was calculated against the fluoride standards calibration curve.

TABLE 11

Stability Testing at Room Temperature (25° Celsius)

| Time (Month) | Appearance | Precipitation after $KH_2PO_4$ | Color Change/ Black Stain |
|---|---|---|---|
| 0 | Clear, faint yellow solution; no undissolved particles. | Yes | No |
| 1 | Same as time 0. | Yes | No |
| 3 | Same as time 0. | Yes | No |
| 6 | Same as time 0. | Yes | No |
| 9 | Clear, slightly darker yellow than time 0; no undissolved particles. | Yes | No |

TABLE 12

Stability Testing at 37° Celsius

| Time (Month) | Appearance | Precipitation after $KH_2PO_4$ | Color Change/ Black Stain |
|---|---|---|---|
| 0 | Clear, faint yellow solution; no undissolved particles. | Yes | No |
| 1 | Same as time 0. | Yes | No |
| 3 | Same as time 0. | Yes | No |
| 6 | Same as time 0. | Yes | No |
| 9 | Clear, slightly darker yellow than time 0; no undissolved particles. | Yes | No |

TABLE 13

Stability Testing at 45° Celsius

| Time (Month) | Appearance | Precipitation after $KH_2PO_4$ | Color Change/ Black Stain | Total Fluoride (ppm) |
|---|---|---|---|---|
| 0 | Clear, faint yellow solution; no undissolved particles. | Yes | No | 25799 |
| 1 | Same as time 0. | Yes | No | Not tested |
| 2 | Same as time 0. | Yes | No | Not tested |
| 3 | Same as time 0. | Yes | No | Not tested |
| 6 | Clear, slightly darker yellow than time 0; no undissolved particles | Yes | No | 27359 |
| 9 | Same as 6 months. | Yes | No | Not tested |

TABLE 14

Stability Testing at 60° Celsius

| Time (Month) | Appearance | Precipitation after $KH_2PO_4$ | Color Change/ Black Stain | Total Fluoride (ppm) |
|---|---|---|---|---|
| 0 | Clear, faint yellow solution; no undissolved particles. | Yes | No | 25799 |
| 0.5 (2 weeks) | Same as time 0. | Yes | No | Not tested |
| 1 | Same as time 0. | Yes | No | 25759 |
| 1.5 (6 weeks) | Same as time 0. | Yes | No | Not tested |
| 2 | Clear, slightly darker yellow than time 0; no undissolved particles | Yes | No | Not tested |
| 2.5 (10 weeks) | Same as 2 months. | Yes | No | Not tested |
| 3 | Same as 2 months. | Yes | No | 27034 |

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An aqueous oral care one-part composition comprising:

13-17 wt-% silver cations;

ammonium iodide present in an amount to provide a molar ratio of silver cations to iodide anions of at least 0.09:1 to less than 0.42:1;

2.25-3.0 wt-% fluoride anions; and water present in an amount of less than 41.2 wt %; and wherein the weight percentages are based on the total weight of the composition.

2. The oral care one-part composition of claim 1 which forms a precipitate upon contact with additional water or saliva.

3. The oral care one-part composition of claim 1 further comprising sodium iodide, potassium iodide, or a combination thereof.

4. The oral care one-part composition of claim 1 further comprising sodium iodide, potassium iodide, silver iodide, or a combination thereof.

5. The oral care one-part composition of claim 1 comprising a source of silver cations selected from silver fluoride, silver chloride, silver nitrate, silver iodide, silver diamine fluoride, and combinations thereof.

6. The oral care one-part composition of claim 1 comprising a source of fluoride anions selected from silver fluoride, silver diamine fluoride, sodium fluoride, ammonium fluoride, potassium fluoride, amine fluoride, and combinations thereof.

7. The oral care one-part composition of claim 1 further comprising a thickener.

8. The oral care one-part composition of claim 1 comprising less than 5 wt-% organic solvent.

9. The oral care one-part composition of claim 1 comprising at least 20 wt-% water, based on the total weight of the composition.

10. The oral care one-part composition of claim 1 further comprising one or more active agents.

11. The oral care one-part composition of claim 1 further comprising calcium cations.

12. The oral care one-part composition of claim 1 further comprising a surfactant.

13. The oral care one-part composition of claim 1 which does not stain teeth.

14. A method of providing fluoride to a patient's tooth surface, the method comprising applying the aqueous oral care one-part composition of claim 1 to the patient's tooth surface.

15. A method of reducing the incidence of dental caries in a patient in need thereof, the method comprising applying an aqueous oral care one-part composition of claim 1 to the patient's tooth surface.

16. A method of reducing dentin sensitivity and/or root sensitivity in a patient in need thereof, the method comprising applying an aqueous oral care one-part composition of claim 1 to the patient's tooth surface.

17. A kit comprising an aqueous oral care one-part composition of claim 1 and an applicator.

* * * * *